(12) United States Patent
Burgess et al.

(10) Patent No.: US 11,040,505 B2
(45) Date of Patent: Jun. 22, 2021

(54) MEDICAL DEVICE

(71) Applicant: Invibio Device Component Manufacturing Limited, Lancashire (GB)

(72) Inventors: Michael Burgess, Lancashire (GB); Steven Lamorlniere, Lancashire (GB)

(73) Assignee: INVIBO COMPONENT MANUFACTURING LIMITED, Lancashire (GB)

( * ) Notice: Subject to any disclaimer, the term of this patent is extended or adjusted under 35 U.S.C. 154(b) by 0 days.

(21) Appl. No.: 15/752,766

(22) PCT Filed: Aug. 11, 2016

(86) PCT No.: PCT/GB2016/052500
§ 371 (c)(1),
(2) Date: Feb. 14, 2018

(87) PCT Pub. No.: WO2017/029476
PCT Pub. Date: Feb. 23, 2017

(65) Prior Publication Data
US 2018/0236736 A1    Aug. 23, 2018

(30) Foreign Application Priority Data
Aug. 17, 2015 (GB) ..................... 1514579

(51) Int. Cl.
*A61L 27/44* (2006.01)
*A61F 2/32* (2006.01)
(Continued)

(52) U.S. Cl.
CPC ............ *B29C 70/70* (2013.01); *A61B 17/846* (2013.01); *A61B 17/866* (2013.01); *A61L 27/28* (2013.01);
(Continued)

(58) Field of Classification Search
CPC ....... B29C 66/71; B29C 64/118; B29C 70/30; B29C 66/721; B29C 33/76; B29C 35/02;
(Continued)

(56) References Cited

U.S. PATENT DOCUMENTS 4,626,306 A    12/1986   Chabrier et al.
5,714,105 A     2/1998   Hansjoerg et al.
(Continued)

FOREIGN PATENT DOCUMENTS

DE    4004472 A1      8/1991
DE    4101226 A1 *    7/1992   ............. B29C 70/34
(Continued)

OTHER PUBLICATIONS

International Search Report and Written Opinion of corresponding International Application No. PCT/GB2016/052500 dated Mar. 1, 2017; 11 pages.
(Continued)

*Primary Examiner* — Ann Schillinger
(74) *Attorney, Agent, or Firm* — Shumaker, Loop & Kendrick, LLP

(57) ABSTRACT

The invention relates to an implantable medical device having a body comprising a composite material. The body has a variable cross section along a length, a first portion which forms a part of a surface of said body, and a packing portion. An insert is provided in the packing portion for providing an increased thickness to at least a part of the body.

10 Claims, 7 Drawing Sheets

(51) Int. Cl.

| | |
|---|---|
| *A61F 2/30* | (2006.01) |
| *B29C 70/70* | (2006.01) |
| *A61B 17/86* | (2006.01) |
| *B29C 70/34* | (2006.01) |
| *A61L 27/28* | (2006.01) |
| *A61B 17/84* | (2006.01) |
| *B29L 31/00* | (2006.01) |
| *A61B 17/00* | (2006.01) |
| *A61B 17/80* | (2006.01) |

(52) U.S. Cl.
CPC .......... *A61L 27/443* (2013.01); *A61L 27/446* (2013.01); *B29C 70/34* (2013.01); *A61B 17/80* (2013.01); *A61B 2017/00526* (2013.01); *A61B 2017/00964* (2013.01); *A61L 2420/04* (2013.01); *A61L 2420/08* (2013.01); *B29L 2031/7532* (2013.01)

(58) Field of Classification Search
CPC ... B29C 45/0001; B29C 48/21; B29C 51/145; B29C 64/153; B29C 65/3656; B29C 66/73115; B29C 66/8122; B29C 70/088; B29C 70/226; B29C 70/228; A61B 2017/00526; A61B 2017/12054; A61B 2090/064; A61B 17/1214; A61B 17/12145; A61B 18/1492; A61L 31/10; A61L 2430/02; A61L 31/048; A61L 31/126; A61L 27/446; A61L 27/46; A61L 27/48; A61L 27/50; A61L 27/58; A61L 2300/00; A61L 2400/06; A61L 2420/08; A61L 27/18; A61L 31/082; A61L 31/146; A61L 31/16; A61L 31/18

See application file for complete search history.

(56) References Cited

U.S. PATENT DOCUMENTS

| | | |
|---|---|---|
| 2009/0223588 A1 | 9/2009 | Dunleavy |
| 2010/0076114 A1* | 3/2010 | Devine .................. A61L 27/18 523/113 |
| 2010/0170988 A1 | 7/2010 | Meyer et al. |
| 2011/0151259 A1* | 6/2011 | Jarman-Smith .......... C08J 3/203 428/402 |
| 2014/0343707 A1* | 11/2014 | Sereno ............... A61C 13/0022 700/97 |
| 2016/0319867 A1* | 11/2016 | Adam .................. F16C 33/201 |

FOREIGN PATENT DOCUMENTS

| | | |
|---|---|---|
| DE | 4101226 A1 | 7/1992 |
| EP | 0102158 A2 | 3/1984 |
| EP | 0102159 A2 | 3/1984 |
| EP | 0572751 A1 | 12/1993 |
| EP | 0592473 B1 | 10/1996 |
| EP | 1092529 A1 | 4/2001 |
| EP | 2402146 A2 | 1/2012 |
| FR | 2951400 A1 | 4/2011 |
| GB | 2471508 A | 1/2011 |
| WO | 9015708 A1 | 12/1990 |
| WO | 9622878 A1 | 8/1996 |
| WO | 2007045913 A2 | 4/2007 |
| WO | 2015057391 A1 | 4/2015 |

OTHER PUBLICATIONS

Search Report for GB1514579.0 dated Feb. 9, 2016 (2 pages).
International Search Report for PCT/GB2016/052500 dated Jan. 3, 2017 (3 pgs,).
Miller et al., "Impregnation Techniques for Thermoplastic Matrix Composites", Polymers & Polymer Composites, vol. 4, No. 7, 1996, pp. 459-481.

* cited by examiner

Prior Art

MEDICAL DEVICE

TECHNICAL FIELD AND BACKGROUND

The present invention relates to an implantable medical device. The invention further relates to a method of manufacturing such a device.

Devices made from polymeric composite material are known. Such material has the advantage over a metal counterpart because it provides improved flexibility to the device whilst maintaining the strength required for load bearing. In addition, implantable polymeric devices are known to be less likely to cause bone deterioration in the patient.

A typical polymeric composite arrangement comprises a plurality of plies of material which are compression molded together. FIG. 1a shows a common lay up configuration for an article having a constant cross section whereby unidirectional plies are orientated in a specific direction with respect to an X axis as indicated in the figure. It is known that when building such an arrangement, consideration must be given to the symmetrical nature of the stack, to minimise bending or warping. However, for devices which have a varying cross section, extra care is needed to achieve the desired thickness at specific locations along the length of the device. Typically, this is achieved by a graduated layered arrangement whereby smaller lengths of plies are placed in a stepped sequence on top of longer lengths of ply as shown in FIG. 1b. Disadvantageously, such an arrangement can lead to shearing or delamination at the exterior facing surface due to the graduated exposed edges; this may lead to device failure or, in medical devices, exposure of filler material to patient tissue.

BRIEF SUMMARY OF THE INVENTION

It is an object of the present invention to provide an implantable medical device having an improved composite structure to minimize the risk of delamination or shearing of the device. It is a further object of the invention to provide an implantable medical device having an improved composite structure to minimize tissue contact with composite filler.

According to an aspect of the present invention there is provided an implantable medical device having a body comprising a composite material, the body having a variable cross section along a length, the body comprising a first portion which forms a part of a surface of said body, and a packing portion, wherein an insert is provided in the packing portion, the insert providing an increased thickness to at least a part of the body.

Preferably, the first portion comprises at least one ply. Preferably, the first portion comprises a first ply and a second ply. Preferably, the first and second plies form a part of the surface of the body. In a most preferred embodiment, the first portion forms substantially the whole of the surface of the body.

In a preferred arrangement, the surface of the body is an exterior facing surface thereof. The exterior facing surface is typically that surface of a medical device that lays adjacent patient bone or tissue in situ.

Preferably, the packing portion is adjacent the first portion. Preferably, the packing portion comprises at least one packing ply, preferably a plurality of packing plies. Said plies may be of the same length as at least one ply of the first portion. Preferably, the plurality of packing plies is configured in a lay-up arrangement, preferably having at least one line of symmetry, preferably about a longitudinal axis of the body. Preferably, the or each packing ply is adjacent the first ply and/or the second ply of the first portion. Preferably, a packing ply is adjacent at least a part of the insert. Most preferably, the or each packing ply is arranged to encase the insert.

Preferably, the insert comprises at least one insert ply. Preferably, a plurality of insert plies is provided. Preferably, the or each insert ply is of a different length to a neighbouring insert ply. Preferably, the or each insert ply is of a different length to the or each packing ply. Preferably, the or each insert ply is of a different length to the first and/or second ply of the first portion. Preferably, the or each insert ply is less than 90% of the length of the or each packing ply, preferably less than 50%, preferably less than 20%. Preferably, the or each insert ply is less than 90% of the length of the or each first or second ply of the first portion, preferably less than 50%.

Preferably, when a plurality of insert plies is provided, said plies are arranged in a randomly stacked configuration. Most preferably, such configuration has no line of symmetry about the longitudinal axis of the body.

In a most preferred arrangement, the insert is substantially wholly encapsulated within the packing portion. Further most preferably, at least one packing ply may be provided between the or each insert ply.

Advantageously, provision of the insert within the packing portion minimises the risk of exposure of filler material to a patient.

Advantageously, the provision of the insert in the packing portion minimises the risk of delamination and reduces the risk of shearing occurring at the surface of the device. This is particularly critical for implantable medical devices which are in contact with tissue or bone.

Preferably, the first portion, and/or the packing portion, and/or the insert comprise composite material.

Preferably, the composite material comprises a fibrous filler and a polymeric material.

The composite material suitably includes at least 30 vol %, more preferably at least 40 vol %, especially at least 50 vol % of the polymeric material. Said composite material may include up to 70 vol %, up to 65 vol %, up to 50 vol % of carbon fibres. Said composite material may include to 50 vol % of said polymeric material and 40 to 65 vol % of carbon fibre. In a preferred embodiment said composite material comprises 40 vol % of polymeric material of formula I.

A preferred polymeric material is a polyaryletherketone having a repeat unit of formula (I)

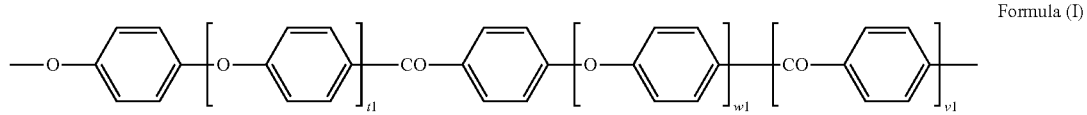

Formula (I)

where t1 and w1 independently represent 0 or 1 and v1 represents 0, 1 or 2.

Said polyaryletherketone suitably includes at least 90, 95 or 99 mol % of repeat unit of formula I.

Said polyaryletherketone preferably consists essentially of a repeat unit of formula I. Preferred polymeric materials comprise (especially consist essentially of) a said repeat unit wherein t1=1, v1=0 and w1=0; t1=0, v1=0 and w1=0; t1=0, w1=1, v1=2; or t1=0, v1=1 and w1=0. More preferred comprise (especially consist essentially of) a said repeat unit wherein t1=1, v1=0 and w1=0; or t1=0, v1=0 and w1=0. The most preferred comprises (especially consists essentially of) a said repeat unit wherein t1=1, v1=0 and w1=0.

In preferred embodiments, said polymeric material is selected from polyetheretherketone, polyetherketone, polyetherketoneetherketoneketone and polyetherketoneketone. In a more preferred embodiment, said polymeric material is polyetheretherketone or PEEK.

In a most preferred embodiment, said composite material comprises 38 wt % of polymeric material of formula I and 62 wt % carbon fibre.

Said polyaryletherketone may have a Notched Izod Impact Strength (specimen 80 mm×10 mm×4 mm with a cut 0.25 mm notch (Type A), tested at 23° C., in accordance with ISO180) of at least 4 KJm$^{-2}$, preferably at least 5 KJm$^{-2}$, more preferably at least 6 KJm$^{-2}$. Said Notched Izod Impact Strength, measured as aforesaid, may be less than 10 KJm$^{-2}$, suitably less than 8 KJm$^{-2}$. The Notched Izod Impact Strength, measured as aforesaid, may be at least 3 KJm$^{-2}$, suitably at least 4 KJm$^{-2}$, preferably at least 5 KJm$^{-2}$. Said impact strength may be less than 50 KJm$^{-2}$, suitably less than 30 KJm$^{-2}$.

Said polyaryletherketone suitably has a melt viscosity (MV) of at least 0.06 kNsm$^{-2}$, preferably has a MV of at least 0.09 kNsm$^{-2}$, more preferably at least 0.12 kNsm$^{-2}$. Said polyaryletherketone may have a MV of less than 1.00 kNsm$^{-2}$, preferably less than 0.5 kNsm$^{-2}$.

Said polyaryletherketone may have a MV in the range 0.09 to 0.5 kNsm$^{-2}$, preferably in the range 0.1 to 0.3 kNsm$^{-2}$, preferably having a MV in the range 0.1 to 0.2 kNsm$^{-2}$. An MV of 0.15 kNsm$^{-2}$ has been found to be particularly advantageous. MV is suitably measured using capillary rheometry operating at 400° C. at a shear rate of 1000 s$^{-1}$ using a tungsten carbide die, 0.5 mm×3.175 mm.

Said polyaryletherketone may be amorphous or semi-crystalline. It is preferably crystallisable. It is preferably semi-crystalline. The level and extent of crystallinity in a polymer is preferably measured by wide angle X-ray diffraction (also referred to as Wide Angle X-ray Scattering or WAXS), for example as described by Blundell and Osborn (Polymer 24, 953, 1983). Alternatively, crystallinity may be assessed by Differential Scanning calorimetry (DSC).

The level of crystallinity of said polyaryletherketone may be at least 1%, suitably at least 3%, preferably at least 5% and more preferably at least 10%. In especially preferred embodiments, the crystallinity may be greater than 25%. It may be less than 50% or less than 40%.

The main peak of the melting endotherm (Tm) of said polyaryletherketone (if crystalline) may be at least 300° C.

The composite material may include one or more further components. It may include up to 15 wt %, preferably up to 10 wt % of other components. An example of another component is an X-ray contrast material for example barium sulphate.

Preferably, each said ply of the first portion and/or packing portion and/or the insert comprises the composite material having a thickness from 10 μm to 1 mm, preferably 100 to 300 μm, most preferably from 140 to 200 μm.

The fibres used in the composite layer may be selected from inorganic fibrous materials and non-melting and high-melting organic fibrous materials, such as aramid fibres, carbon fibre and the like. For instance, the fibres may be selected from glass fibre, carbon fibre, silica fibre, zirconia fibre, silicon nitride fibre, boron fibre, fluorocarbon resin fibre and potassium titanate fibre. Most preferred fibres are carbon fibres. Nanofibres may be employed.

Preferably, a coating is provided on the body. Preferably, the coating is adjacent at least a part of the first portion. Preferably, the coating comprises a first coating layer and a second coating layer. Preferably, the first coating layer is provided on an upper surface of the body. Preferably, the second coating layer is provided on a lower surface of the body. Preferably, the first coating layer is remote from the second coating layer. Preferably, the first coating layer does not touch the second coating layer.

In a preferred embodiment, the first and second coating layers are separate from each other such that the first coating layer forms an upper face of the device and the second coating layer forms a lower face of the device. The ends of the device body are substantially free of both the first and second coating layers. The coating may form substantially the whole of the exterior surface.

Preferably, the or each coating layer is between 10 μm and 1 mm thickness. Preferably, the or each layer is between 100 μm and 600 μm, most preferably substantially 200 μm. Thicknesses are suitably as measured by a film thickness gauge such as a Hanatek FT3 gauge.

The coating is preferably a radiopaque material which may be any material which when added to a polymeric material increases the radiopacity of the combination. Said radiopaque material preferably improves the imageability of the first polymeric material when imaged using both CT and MRI techniques. Said radiopaque material may comprise a metal, an inorganic material or an iodine-containing organic material.

Preferably, the coating comprises barium sulphate and a polyaryletherketone. Most preferably, the polyaryletherketone is PEEK.

Preferably, the coating includes at least 1 wt %, suitably at least 2 wt %, preferably at least 3 wt % barium sulphate. Preferably, the amount of barium sulphate is between 6 wt % and 60 wt %. In a preferred embodiment, the or each, preferably both, said coating layers comprise substantially 20 wt % barium sulphate.

Said barium sulphate is preferably intimately mixed with the PEEK polymer, suitably so the barium sulphate and said polymer define a substantially homogenous mixture.

Said PEEK in the or preferably each coating layer suitably has a melt viscosity (MV) of at least 0.06 kNsm$^{-2}$, preferably has a MV of at least 0.09 kNsm$^{-2}$, more preferably at least 0.12 kNsm$^{-2}$. Preferably, said PEEK has a MV between 0.1 and 0.5 kNsm$^{-2}$. Preferably, the PEEK has an MV between 0.35 and 0.45 kNsm$^{-2}$.

Said PEEK may have the same MV as the composite polymeric material of the first portion and/or the packing portion, and/or the insert.

Preferably, the or each coating layer includes less than 10 wt % of fibres, for example less than 5 wt % or less than 0.5 wt %. It preferably includes no fibres. Said coating may be made by any suitable means known in the prior art, such as by melt extrusion of the polymer through a wide, T-shaped film die with adjustable gap. The or each coating layer may be a metal foil, for example comprising titanium, tungsten or zirconium oxide. Preferably, the implantable medical device is a plate, or a nail or a screw. The implantable medical device is most preferably an implantable trauma plate for fracture fixation.

According to a second aspect of the invention, there is provided a method of manufacturing an implantable medical device having a body comprising a composite material, the body having a variable cross section along a length, the body comprising a first portion having at least a first ply and a second ply, a packing portion having at least one packing ply, and an insert having at least one insert ply, wherein the method comprises the following steps:

(a) Arranging the first ply of the first portion to form a first surface of a lay-up arrangement;
(b) Applying a first packing ply to the first ply;
(c) Applying at least one insert ply to the first packing ply;
(d) Applying a second packing ply to the at least one insert ply;
(e) Applying a second ply of the first portion to the second packing ply; and
(f) Molding the lay-up arrangement.

Preferably, the first surface is an exterior facing surface of the device. Preferably, the second ply forms a second exterior facing surface of the device.

Preferably, the molding step (f) is a compression molding step. Preferably, step (f) takes place at temperatures between 350° C. and 400° C., preferably between 350 and 380° C., most preferably between 350° C. and 370° C.

Preferably, the method comprises a step (g) which takes place after step (f) wherein the body is rapidly cooled, preferably to between 140° C. and 200° C.

Preferably, the method includes a further step (h) of applying a coating comprising a first coating layer and a second coating layer to the device. Preferably, the coating layer comprises a radiopaque marker, most preferably barium sulphate as hereinbefore described. Preferably, the coating step (h) takes place after step (e). The coating may be applied after step (f). Preferably, the method includes a further molding step (i) for molding the coating to the layup to provide the finished device.

Preferably, the first coating layer and the second coating layer are remote from each other. In this manner, advantageously, a radiopaque marker is provided on the surface of the device.

Preferably, step (i) takes place under pressure, preferably between 2 and 8 MPa. Preferably, the molding step takes place at temperatures between 340° C. and 400° C., most preferably between 350° C. and 370° C.

Preferably, the method further includes a step of trimming the device obtained from the or each molding step (f) or (i) to remove any flashing.

Preferably, the method is carried out by an automated process.

According to a further aspect of the present invention there is provided an implantable medical device having a body comprising a composite material, the body having a variable cross section along a length, the body comprising a first portion, a packing portion, and a coating, the coating forming at least part of an exterior surface of the body, wherein an insert is provided in the packing portion, the insert providing an increased thickness to at least a part of the body.

Preferably, the coating includes at least 1 wt %, suitably at least 2 wt %, preferably between 6 and 60 wt % barium sulphate.

Preferably, the device comprises an additional material operable to reduce bacterial activity, or to encourage bone growth. The material may be porous titanium or hydroxyapatite. Said material may be in the form of a layer of film.

All of the features described herein may be combined with any one of the above aspects, in any combination.

BRIEF DESCRIPTION OF THE DRAWINGS

An embodiment of the invention will now be described, by way of example only, with reference to the accompanying drawings, wherein.

DETAILED DESCRIPTION OF THE INVENTION

Figure 1A:
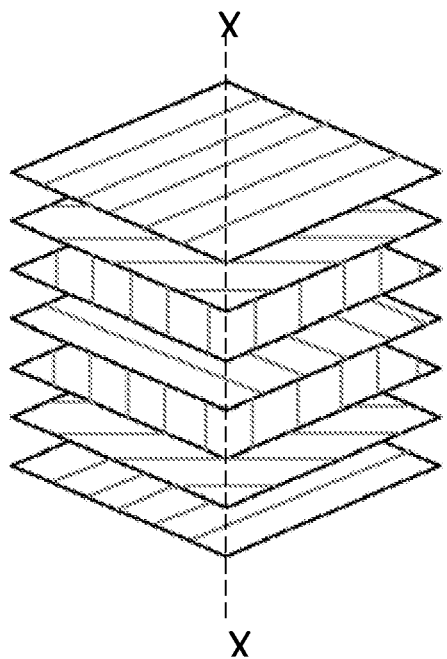
FIG. 1a shows a schematic perspective view of a typical composite lay up arrangement.
Figure 1B:
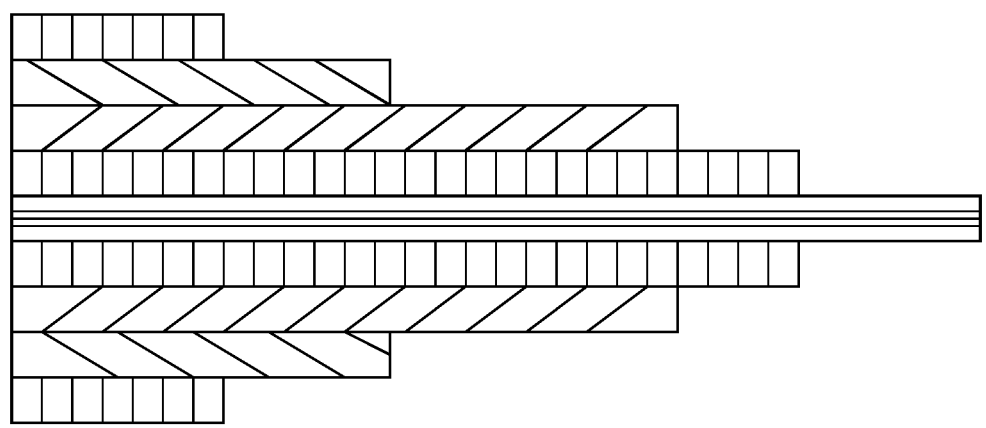
FIG. 1b shows a schematic sectional side view of a further typical composite lay up arrangement.
Figure 2:
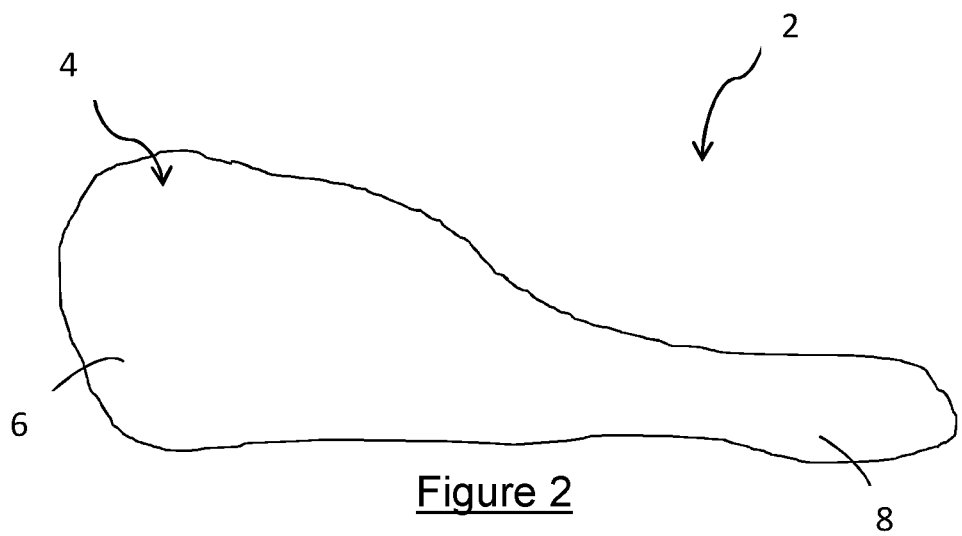
FIG. 2 shows a schematic side view of a medical device according to the present invention.

Figures 1a and 1b show typical lay-up arrangements as previously discussed. FIG. 2 shows a device 2 according to the present invention. The device 2 is an implantable medical device that comprises a body 4 having a head 6 and a tail 8. It can be seen that the cross sectional area of the device 2 varies along the longitudinal length of the body 4, with the head 6 being much greater in thickness compared to the tail 8.

The device 2 comprises a first portion 10, a packing portion 12 and an insert 14. The first portion 10 includes a first ply 16 and a second ply 18. The first and second plies 16,18 together form the exterior surface of the device 2.

Figure 3:
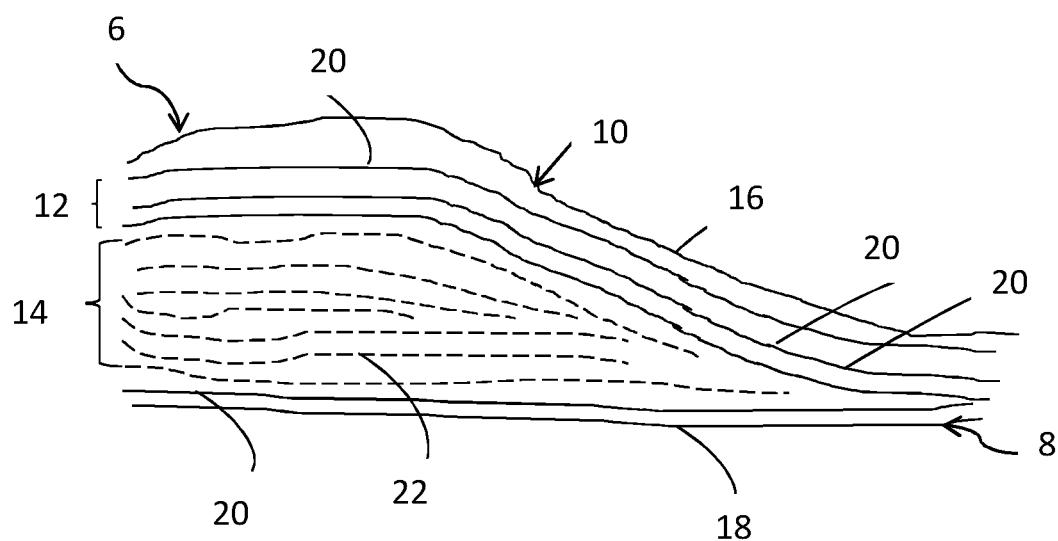
FIG. 3 shows a schematic sectional side view of a part of the medical device of FIG. 2.

The packing portion 12 comprises a plurality of packing plies 20 which are adjacent the inner face of the first portion 10. As shown in FIG. 3, the packing plies 20 are located either side of the insert 14, and adjacent the first and second plies 16,18. The packing plies 20 are symmetrical about the longitudinal axis of the body 4. In an alternative embodiment, packing plies are provided between insert plies.

The insert 14 comprises at least one insert ply 22. In the embodiment shown in FIG. 3, a plurality of insert plies 22 (represented by dashed lines) is provided in the device 2. The or each insert ply 22 is shorter in length when compared to the packing plies 20. In so doing, the packing plies 20 surround the insert 14, encasing it within the packing portion 12 as shown most clearly in FIG. 6b.

Figure 4:
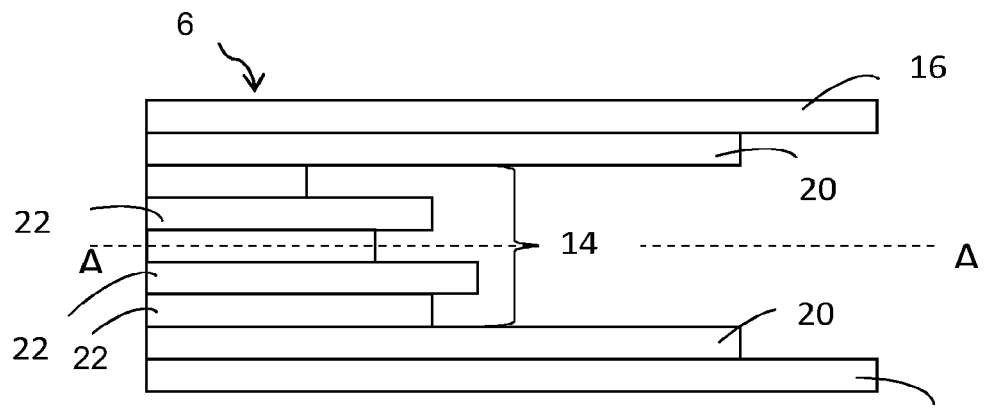
FIG. 4 shows an embodiment of a lay-up arrangement of part of a device according to the present invention.
Figure 5:
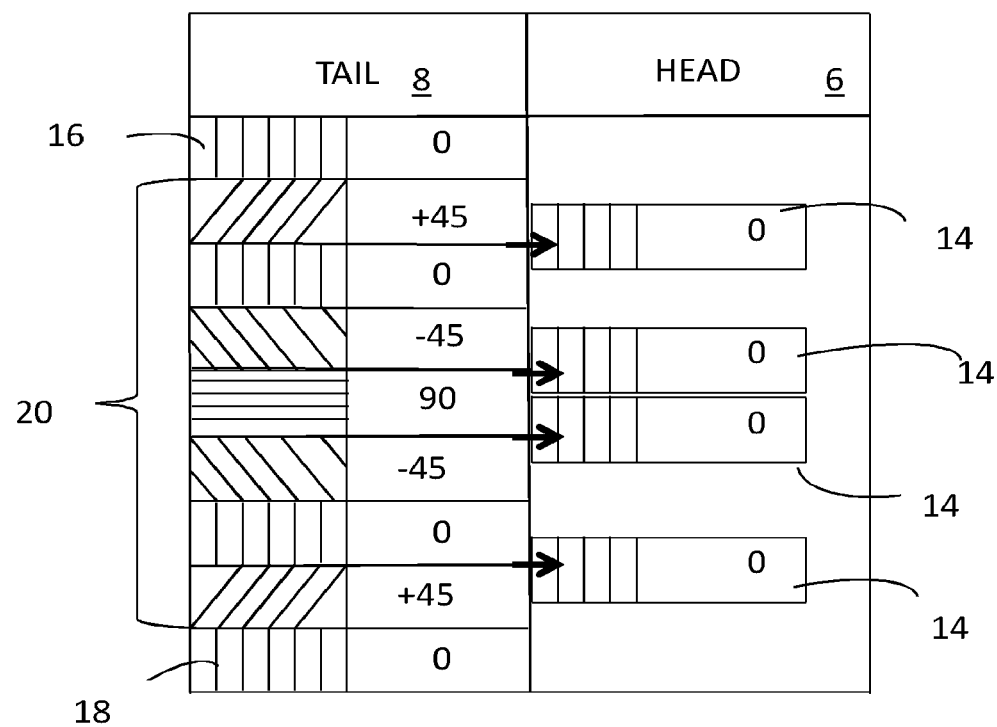
FIG. 5 shows an embodiment of a lay-up arrangement of a device according to the present invention.

An embodiment of a lay-up arrangement of the head 6 of the medical device 2 is shown in greater detail in FIGS. 4 and 5. In FIG. 4, the first ply 16 and second ply 18 form the exterior facing surface of the body 4. Packing plies 20 are located adjacent said first and second plies 16,18. The insert 14 is located between the packing plies 20. It can be seen, that the insert plies 22 are non-symmetrical about an axis A, being of varying lengths to one another, and each being shorter in length than the adjacent packing ply 20. Provision of a non-symmetrical layering of the insert plies 22 ensures a greater degree of consistency in the overall cross section required by the head 6.

FIG. 5 shows the lay-up arrangement of the plies, with respect to the X axis, in the head 6 and tail 8. Specifically, in the tail 8, the first and second plies 16, 18 are placed at 0°, and the packing plies 20 are orientated at +45°, 0°, −45°, 0°, 90°, −45°, 0°, +45°. The head 6 has a greater thickness than the tail 8 and so inserts 14 are provided within the packing portion 20 at locations indicated by the arrows in the figure. Each insert 14 is orientated at 0°.

Such an arrangement achieves both the required cross sectional area required by the varying thickness of the device but also, essentially, ensures that the surface of the device comprises complete plies in contrast to the device shown in FIG. 1b. In so doing, the risk of delamination or shearing occurring at the exterior surface of the device 2 is minimised.

Figure 6A:
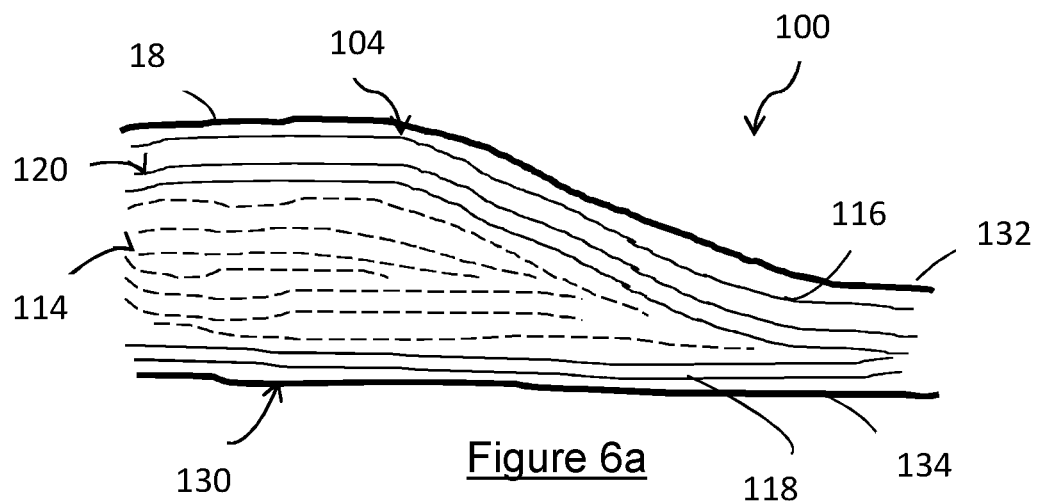
FIGS. 6a and 6b show schematic sectional side views of a device according to the present invention.
Figure 6B:
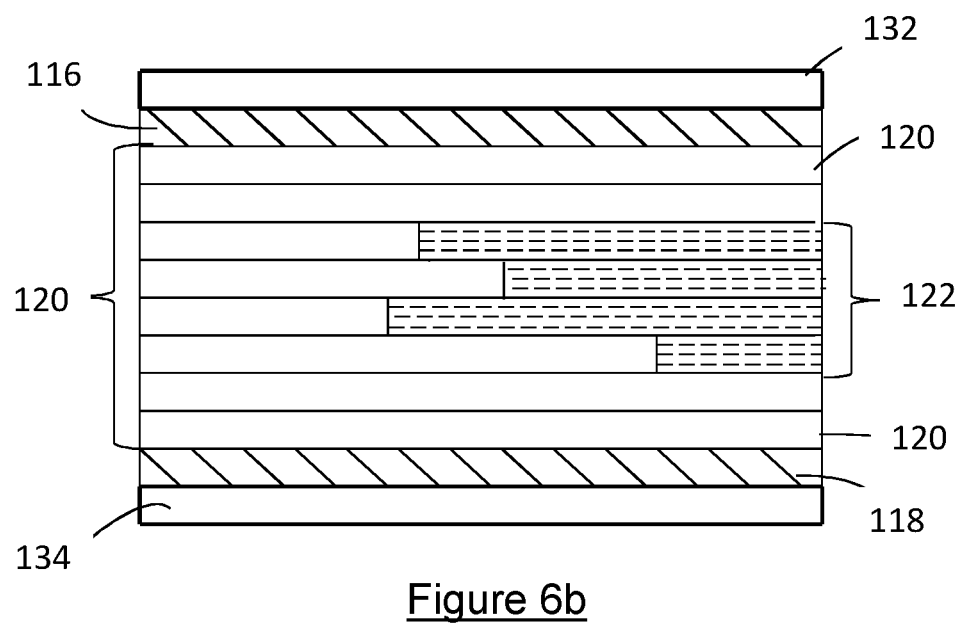

FIG. 6 show an embodiment of a medical device 100 according to the invention. It will be understood by the reader that like reference numerals have been used to reference like parts shown in the previous figures. The device 100 comprises a body 104 having a first portion 110, a packing portion 120, and an insert 114. A coating 130 is located on the first portion 110. The coating 130 comprises a first coating layer 132 and a second coating layer 134. The first coating layer 132 lays adjacent the first ply 116, and the second coating layer 134 lays adjacent the second ply 118. Said coating layers 132, 134 do not extend around the whole surface of the body 104 but cover only an upper surface and a lower surface thereof. FIG. 6a shows that the layup arrangement provided by the invention ensures that the insert 114 is fully encased by the packing plies 120.

The coating 130 comprises a barium sulphate/PEEK composite as will be described in further detail below.

The plies of composite material of PEEK and carbon fibres which make up the body 4, 104 are prepared according to the following method:

General Procedure for Preparing Polyetheretherketone Carbon Fibre Composites

The carbon fibre was an IM7 12K tow from Hexcel Inc. The carbon fibre ply is 62% by weight of carbon fibre, 38% by weight of PEEK-OPTIMA® Natural LT3 obtained from Invibio Biomaterial Solutions Ltd, with a Tm of 340° C. and MV of 0.15. MV is measured using capillary rheometry operating at 400° C. at a shear rate of 1000 s$^{-1}$ using a circular cross-section tungsten carbide die of 0.5 mm capillary diameter×3.175 mm capillary length.

Assembly of Lay-Up Arrangement

Modelling data was generated using Dassault Systems CATIA™ software, to provide an indication of composite lay-up. The plies of the first portion, the packing portion and the insert were then cut. The plies were then assembled according to an embodiment of the invention shown in FIG. 5 wherein a second ply 18, 118 of the first portion 10,110 was orientated and positioned to form a lower surface of the device; a first plurality of packing plies 20,120 were placed on top of the second ply 18,118; the insert plies 22,122 were then positioned within said plurality 20,120 such that the insert plies 22,122 were encapsulated therein; and a first ply 16,116 of the first portion 10,110 was positioned on top of the plurality to form an upper surface of the body 4,104. The lay-up arrangement was compression molded using a PEI Lab Compression Moulder at 370° C.@2 Mpa press force then rapidly cooled under pressure. The laminated device 2,100 was then removed from the mold and machined as required.

General Procedure for Preparing Polyetheretherketone/Barium Sulphate Composites

The coating 130 comprises substantially 20% barium sulphate which is intimately mixed with PEEK polymer having an MV of 0.45 kNsm$^{-2}$ commercially available from Invibio Limited, UK under the trade mark PEEK-OPTIMA Image Contrast. Each layer of the coating is substantially 200 µm in thickness. The barium sulphate used was grade 10175, extra pure for X-ray diagnosis, from Merck.

Barium sulphate was added to PEEK-OPTIMA via an extrusion compounding process. By way of example, the barium sulphate can be gravimetrically metered and fed through a side feeder into a twin screw extruder, where it is combined with plasticized polymer melt and intimately mixed to provide a uniform dispersion of the filler within the polymer. The barium sulphate was added to 20% by weight of the polymer. Extrusion of this mixture through a die generates strands or laces that cool and solidify before being chopped into small granules in preparation for subsequent processing. In the present invention, the composite layer 130 is made into a tape in a conventional manner. For example, the manufacture of tapes is described in, for instance, U.S. Pat. No. 4,626,306 where an aqueous dispersion impregnation method is set out. Other descriptions for the formation of such tapes may be found in "Impregnation Techniques for Thermoplastic Matrix Composites"—A Miller and A G Gibson, Polymer & Polymer Composites 4 (7) 459-481 (1996), in patent application publication EP 0592473 A1 and specifically for melt impregnation in the patent application publications EP 0102158 A2 or EP 0102159 A2.

Addition of Barium Sulphate Coating Tape

A 200 µm tape as prepared above was placed on a base and an upper face of the body so as to sandwich the body therein. The body was placed in a compression mold tool and heated to 360° C. under a pressure of 2 KN. Once the temperature was reached, the mold tool temperature was dropped to 220° C. at a controlled cooling rate using thermocouples to monitor the temperature. The finished device was removed from the mold tool and trimmed to remove unwanted flashing.

Figure 7A:
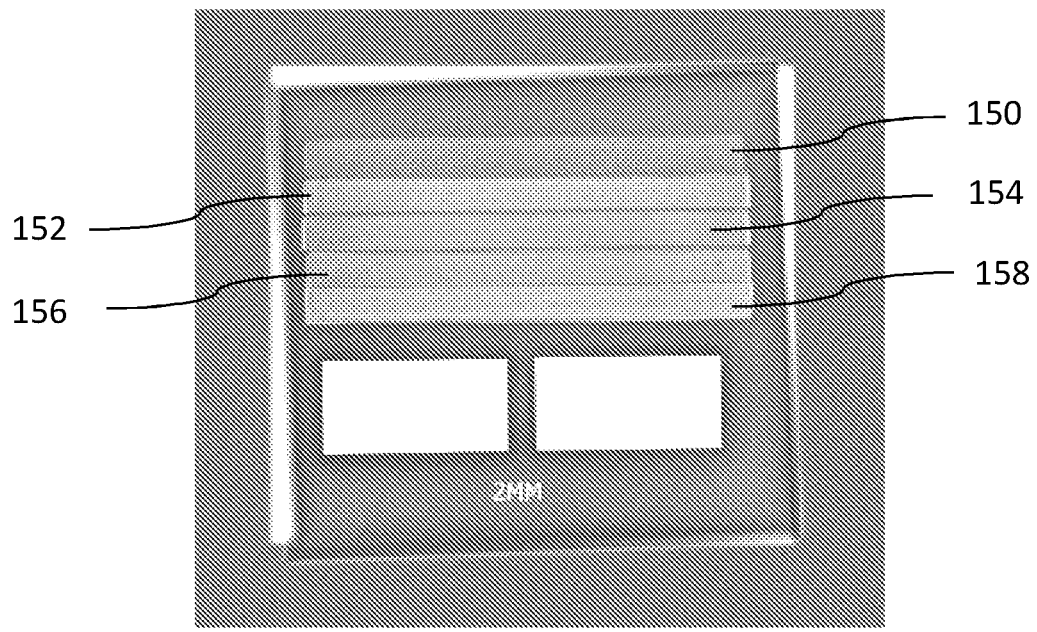
FIGS. 7a and 7b are X-ray images of a 2 mm plate and a 5 mm plate respectively, in accordance with the present invention.

FIG. 7a shows an X-Ray images of five 2 mm composite plates made according to the above procedure for preparing PEEK carbon fibre composites. Plate 150 is a reference plate having no barium sulphate film coating. Plate 152 is a PEEK composite having a 100 µm barium sulphate coating layer, made according to the above, deposited on either side of the plate (total film thickness 0.2 mm). Plate 154 has a 200 µm barium sulphate coating layer (total 0.4 mm); plate 156 has a 300 µm coating layer (total 0.6 mm) and plate 158 has a 400 µm coating layer (total 0.8 mm).

It can be seen that plate 158 having the 400 µm film on either side of the plate provides the brightest contrast as would be expected. However, such a contrast removes the advantage of a clinician being able to view a fracture through the device. Further, such a thickness of barium sulphate reduces the mechanical properties of the overall device which has a restricted overall thickness for implantation; the thicker the barium sulphate layers means that less composite layers can be used in the overall structure. The images show a sufficient contrast when using 200 µm coating layer either side of the body—plate 154.

Figure 7B:
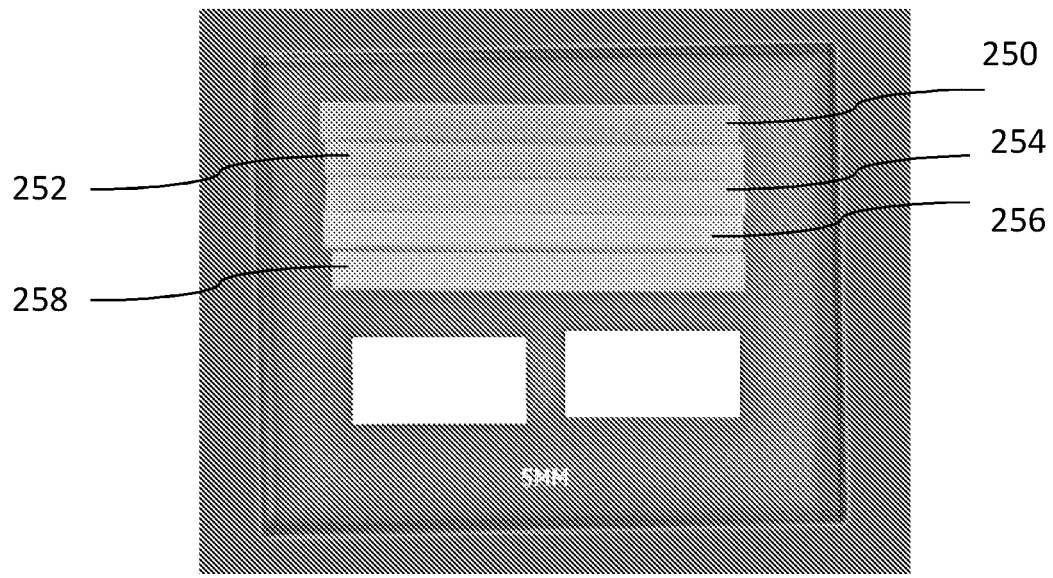

FIG. 7b shows a 5 mm plate with the same layup to those of FIG. 7a. Plate 254 has the 200 μm barium sulphate film either side of the body; this shows sufficient contrast needed for medical use.

Figure 8A:
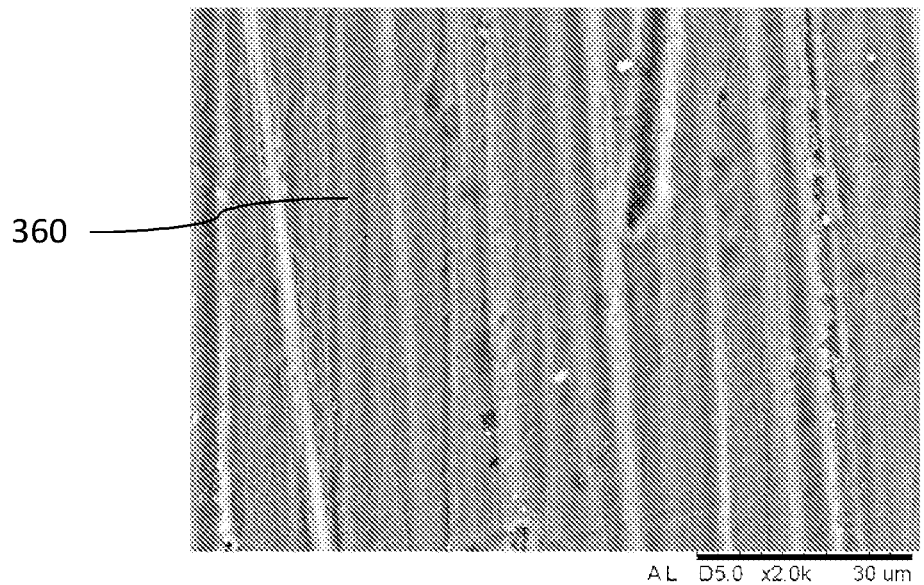
FIGS. 8a and 8b show SEM images of part of a device according to the invention.
Figure 8B:
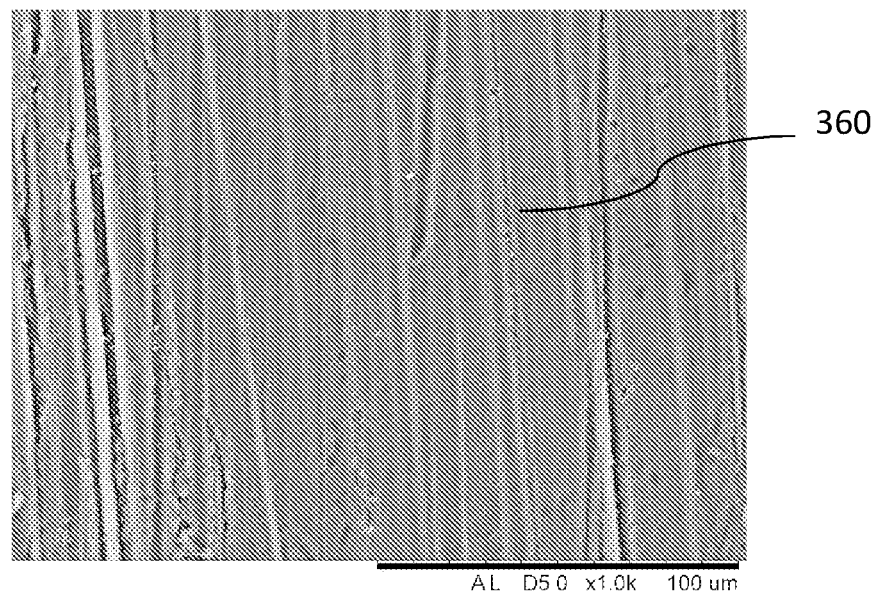
Figure 9A:
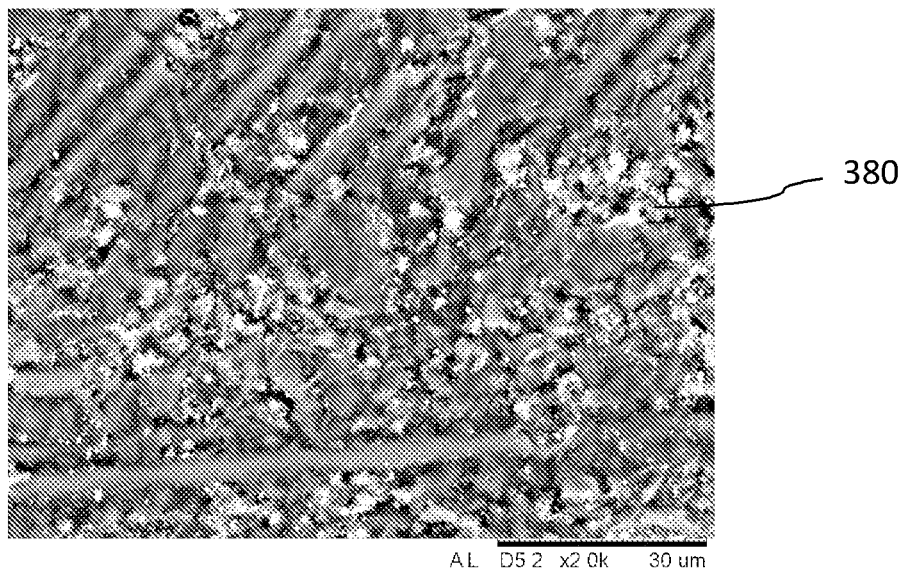
FIGS. 9a and 9b show SEM images of part of a prior art device.
Figure 9B:
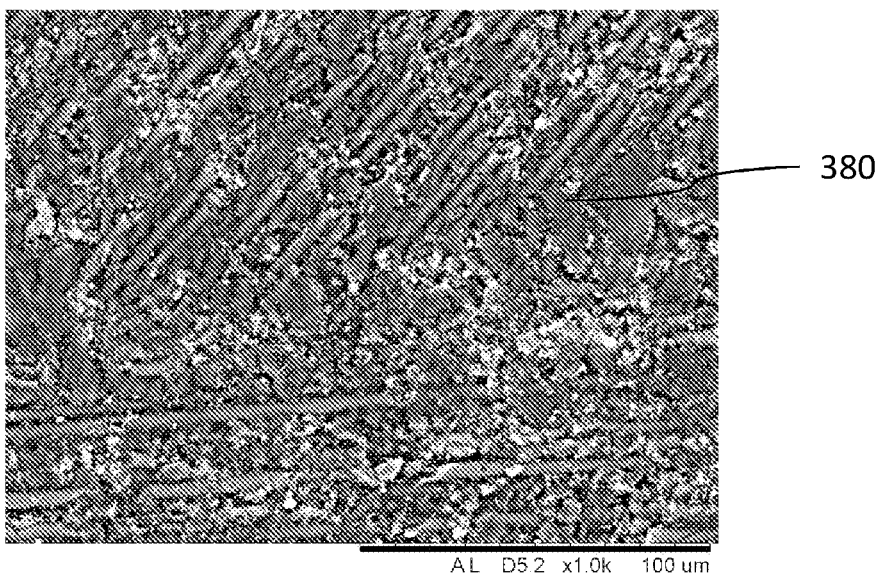

FIGS. 8a and 8b show SEMs (taken using a Hitachi TM300 15KV) of a device according to the present invention without a barium sulphate film. As discussed, due to the insert being encased within the packing portion, the exterior surface 360 of the device comprises a complete length of composite ply which extends over the body. The SEMs show a smoothed surface. Consequently, the risk of shearing of the exterior surface is greatly minimised which in turn reduces the risk of carbon fibre exposure. In contrast, FIGS. 9a and 9b show SEMs (taken using a Hitachi TM300 15KV) of a typical prior art device. In particular, it is shown that an exterior surface 380 of a device, formed by graduated plies as shown in FIG. 1b, has a sheared or serrated finish. It can be seen that the carbon fibre in the composite is exposed.

Advantageously, the lay-up arrangement as hereinbefore described allows for the creation of a device of variable cross section, which minimises the risk of shearing at an exposed surface.

Provision of a radiopaque coating enables greater visibility of a medical implant by medical imaging techniques during and following implantation. During implantation, this assists the surgeon in, for example, screw placement. In addition, the surgeon is able to assess location of the device and be alert to possible breaks in the device.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

What is claimed is:

1. An implantable medical device having:
    a body comprising a composite material comprising polyetheretherketone (PEEK) and
    a lay-up configuration having a plurality of plies of composite material, each of the plies being oriented in a specific fiber direction with respect to an axis,
    the body having:
        a coating comprising:
            barium sulphate in the amount of 6 wt % to 60 wt %; and
            a PEEK polyaryletherketone,
        a variable cross section along a length,
        a first portion which forms a part of a surface of said body, and
        a packing portion, wherein an insert is provided in the packing portion, the insert providing an increased thickness to at least a part of the body,
    wherein the PEEK has a melt viscosity (MV) of at least 0.06 kNsm$^{-2}$, and less than 0.5 kNsm$^{-2}$, wherein the melt viscosity is measured using capillary rheometry operating at 400° C. at a shear rate of 1000 s$^{-1}$ using a tungsten carbide die, 0.5 mm×3.175 mm,
    wherein the composite material comprises carbon fibers, wherein an amount of carbon fibers in the composite material is ≤70 vol %, the composite material comprising barium sulphate wherein barium sulphate in the composite material is in the amount of ≤15 wt %.

2. A device as claimed in claim 1, wherein the first portion comprises a first ply and a second ply of the plurality of plies, said plies forming substantially the whole of the surface of the body.

3. A device as claimed in claim 1, wherein the packing portion is adjacent the first portion, the packing portion comprising at least one packing ply of the plurality of plies.

4. A device as claimed in claim 3, wherein each packing ply is adjacent at least a part of the insert.

5. A device as claimed in claim 1, wherein the insert is substantially wholly encapsulated within the packing portion.

6. A device as claimed in claim 1, wherein the insert comprises at least one insert ply of the plurality of plies.

7. A device as claimed in claim 6, wherein each insert ply is of a different length to a neighboring insert ply.

8. A device as claimed in claim 6, wherein a plurality of insert plies is arranged in a randomly stacked configuration, wherein such configuration has no line of symmetry about the longitudinal axis of the body.

9. A device as claimed in claim 1, wherein the coating is adjacent at least a part of the first portion.

10. A device as claimed in claim 1, wherein a first coating layer is remote from a second coating layer.

* * * * *

UNITED STATES PATENT AND TRADEMARK OFFICE
CERTIFICATE OF CORRECTION

PATENT NO. : 11,040,505 B2  
APPLICATION NO. : 15/752766  
DATED : June 22, 2021  
INVENTOR(S) : Michael Burgess and Steven Lamoriniere Page 1 of 1

It is certified that error appears in the above-identified patent and that said Letters Patent is hereby corrected as shown below:

On the Title Page

Item (72) should read:
(72) Inventors: Michael Burgess, Lancashire (GB)
                 Steven Lamoriniere, Lancashire (GB)

Item (30) - please correct the number of the Foreign Application Number to read:
(30)     Foreign Application Priority Data  
August 17, 2015        (GB)    1514579.0

Signed and Sealed this  
Third Day of August, 2021

Drew Hirshfeld  
*Performing the Functions and Duties of the*  
*Under Secretary of Commerce for Intellectual Property and*  
*Director of the United States Patent and Trademark Office*